(12) United States Patent
Griffiths et al.

(10) Patent No.: US 7,291,760 B2
(45) Date of Patent: *Nov. 6, 2007

(54) PROCESS FOR THE PRODUCTION OF OLEFINS

(75) Inventors: David Charles Griffiths, Surrey (GB); Ian Raymond Little, Surrey (GB); Brian Edward Messenger, Hampshire (GB); Ian Allan Beattie Reid, London (GB)

(73) Assignee: Ineos Europe Limited, Hampshire (GB)

( * ) Notice: Subject to any disclaimer, the term of this patent is extended or adjusted under 35 U.S.C. 154(b) by 0 days.

This patent is subject to a terminal disclaimer.

(21) Appl. No.: 11/602,206

(22) Filed: Nov. 21, 2006

(65) Prior Publication Data

US 2007/0078288 A1 Apr. 5, 2007

Related U.S. Application Data

(63) Continuation of application No. 10/332,800, filed as application No. PCT/GB01/03005 on Jul. 4, 2001, now Pat. No. 7,169,962.

(30) Foreign Application Priority Data

Jul. 11, 2000 (GB) .................................. 0017075.3

(51) Int. Cl.
*C07C 4/02* (2006.01)
*C07C 5/333* (2006.01)

(52) U.S. Cl. ...................... 585/651; 585/652; 585/653; 585/661

(58) Field of Classification Search ................ 585/648, 585/650–653, 658, 661–663
See application file for complete search history.

(56) References Cited

U.S. PATENT DOCUMENTS

| 5,382,741 | A | 1/1995 | Astbury et al. .............. 585/652 |
| 5,654,491 | A | 8/1997 | Goetsch et al. | |
| 7,169,962 | B2 * | 1/2007 | Griffiths et al. ............. 585/651 |

FOREIGN PATENT DOCUMENTS

| EP | 0 332 289 | 9/1989 |
| WO | WO 94/04632 | 3/1994 |
| WO | WO 0015587 | 3/2000 |
| WO | WO 00/37399 | 6/2000 |

* cited by examiner

*Primary Examiner*—Glenn Caldarola
*Assistant Examiner*—In Suk Bullock
(74) *Attorney, Agent, or Firm*—Nixon & Vanderhye

(57) ABSTRACT

A process for the production of an olefin comprising partially combusting in a reaction zone a mixture of a hydrocarbon and an oxygen-containing gas in the presence of a catalyst which is capable of supporting combustion beyond the fuel rich limit of flammability to produce the olefin, wherein the superficial feed velocity of said mixture is at least 250 cm s?-1? at standard temperature and operating pressure with the proviso that where the catalyst is an unsupported catalyst, the superficial feed velocity of said mixture is at least 300 cm s$^{-1}$ at standard temperature and operating pressure.

20 Claims, 1 Drawing Sheet

Key: • Thermocouples

PROCESS FOR THE PRODUCTION OF OLEFINS

Figure 1:
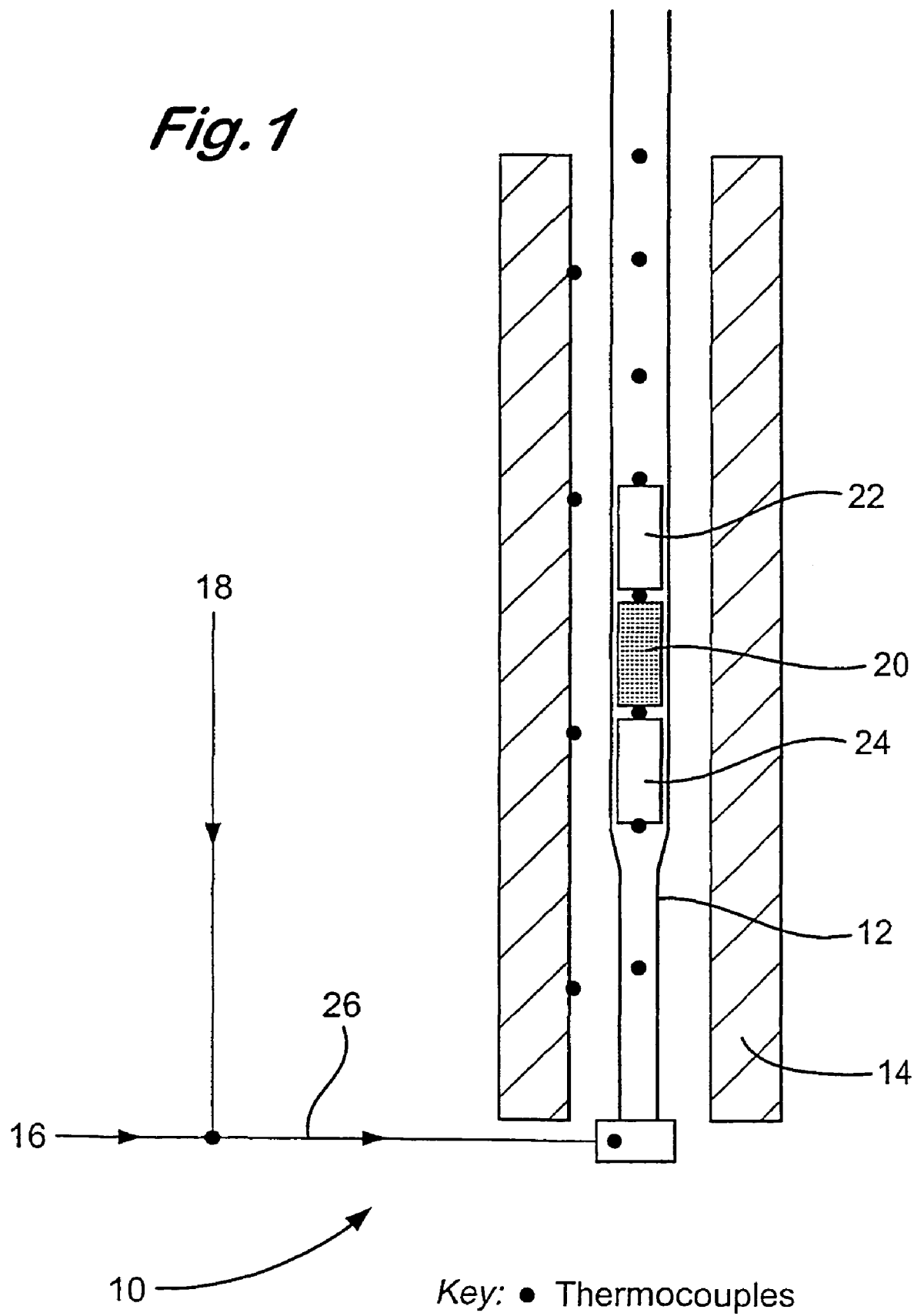

This application is a continuation of application Ser. No. 10/332,800, filed Jun. 16, 2003, now U.S. Pat. No. 7,169,962, which is a 371 of PCT/GB01/03005, filed Jul. 4, 2001, the entire content of which is hereby incorporated by reference in this application.

The present invention relates to a process for the production of olefins from a hydrocarbon feed and, in particular, to a process for the production of olefins by the partial combustion of a hydrocarbon feed.

Olefins such as ethylene and propylene may be produced by the catalytic dehydrogenation of a hydrocarbon feed or the cracking of a hydrocarbon feed. The term "cracking" will be used throughout this specification to embrace both of these chemical reactions.

The cracking of hydrocarbons is an endothermic process. Accordingly, heat has to be consumed for the reaction to occur. Auto-thermal cracking is a known process for the production of olefins from a reactant mixture comprising a hydrocarbon feed and an oxygen-containing gas. An example of an auto-thermal cracking process is described in EP-A-0 332 289.

In an auto-thermal cracking process, the heat required for cracking is generated by combusting a portion of the original hydrocarbon feed. This is achieved by passing a mixture of a hydrocarbon feed and an oxygen-containing gas over catalyst capable of supporting combustion beyond the fuel rich limit of flammability. The hydrocarbon feed is partially combusted, and the heat produced by the combustion reaction is used to drive the cracking of the remainder of the feed into olefins. Optionally, a hydrogen co-feed is also burned, and the heat produced by this combustion reaction is also used to drive the cracking of the hydrocarbon.

In an auto-thermal cracking process, the time for which the reaction mixture (hydrocarbon and an oxygen-containing gas) is in contact with the catalyst (the contact time) is believed to have an impact on the olefin yield of the overall process. Olefin yield is determined by the selectivity of the process towards olefins and the extent of hydrocarbon conversion. For high olefin yields, high selectivity and high conversion are desirable. In general, the conversion of hydrocarbon increases as the contact time increases. Without wishing to be bound by any theory, it is believed that this is because there is more time available for the hydrocarbon to react. However, increasing the contact time tends to have a detrimental effect on the selectivity to olefin, as there is more time for the olefin produced to take part in further (undesirable) reactions.

An indication of contact time can be obtained by measuring the linear velocity of the feed gases upstream from the catalyst at standard temperature (273 Kelvin) and the operating pressure of the process. This measurement, known as the superficial feed velocity, is measured in centimetres per second (cm s$^{-1}$). The higher the superficial feed velocity, the shorter the contact time of the feed for a given catalyst quantity and aspect ratio.

Conventional understanding thus indicates that if high superficial feed velocities are employed in an auto-thermal cracking process the hydrocarbon feed conversion and olefin yield would be significantly reduced. Indeed, it would be expected that conversion and olefin yield would be reduced to such an extent that any potential benefits associated with operation at high superficial feed velocities would be negated.

This teaching has been exemplified by prior art catalytic oxidative dehydrogenation processes. Prior art catalytic oxidative dehydrogenation processes have been operated at superficial feed velocities of up to 265 cm s$^{-1}$, but, more typically, such processes are operated at superficial feed velocities of less than 180 cm s$^{-1}$.

U.S. Pat. No. 5,639,929 discloses an oxidative dehydrogenation process using a fluidised bed catalyst of Pt, Rh, Ni or Pt—Au supported on $\alpha$-Al$_2$O$_3$ or ZrO$_2$ and total feed flow rates of 0.5 to 2.0 SLPM (standard litres per minute) corresponding to superficial feed velocities of ~1 to ~4.1 cm s$^{-1}$ at standard temperature and operating pressure.

U.S. Pat. No. 5,905,180 discloses a catalytic oxidative dehydrogenation process wherein the total feed flow rates "ranged from 5 SLPM", corresponding to a superficial feed velocity of ~24 cm s$^{-1}$ at standard temperature and operating pressure.

Schmidt et al (J. Catal., 191, 62-74 (2000)) describes an oxidative ethane oxidation over a Pt—Sn/$\alpha$-Al$_2$O$_3$ catalyst at a total feed flow rate (ethane, hydrogen and oxygen reactive components, nitrogen diluent) of 4 to 16 standard litres per minute (SLPM), corresponding to a superficial feed velocity of ~22 to ~88 cm s$^{-1}$ at standard temperature and operating pressure. A small fall in ethylene yield was reported on raising the gas flow to the higher figure.

Holmen et al, Studies in Surf. Sci. and Catal., 119, 641-646 (1998) disclose the use of Pt and Pt/Rh gauze catalysts for oxidative ethane dehydrogenation. Experiments were conducted at a total gas feed rate of 2 standard litres per minute over a Pt/Rh gauze (which corresponds to superficial velocities up to ~265 cm s$^{-1}$ at standard temperature and operating pressure). Although they report that the formation of olefins (selectivity) is favoured by short contact times, they also note that conversion was reduced at high velocities when compared with results at ~19 cm s$^{-1}$ unless more heat was applied to the reactor externally.

WO 00/14035 discloses a process for the partial oxidation of paraffinic hydrocarbons to form olefins. The process is carried out in the presence of hydrogen and the use of gas hourly space velocities of greater than 50,000 h$^{-1}$ to generally less than 6,000,000 h$^{-1}$ is disclosed. In one example there is disclosed the partial oxidation of ethane in the presence hydrogen and a ceramic supported Pt/Cu catalyst at gas feed rates of up to 42 standard litres per minute and at a pressure of 1.68 bara. This corresponds to superficial feed velocities up to ~164 cm s$^{-1}$ at standard temperature and operating pressure.

U.S. Pat. No. 4,940,826 discloses a catalytic oxidative dehydrogenation process with a hydrocarbon stream consisting of ethane, propane or butane or mixtures thereof over platinum supported on cordierite monolith or over a bed of platinum on alumina spheres. The total feed flow rates range from 16.0 to 55.0 standard litres per minute corresponding to superficial feed velocities of ~45 to ~180 cm s$^{-1}$ at standard temperature and operating pressure.

U.S. Pat. No. 5,382,741 discloses a catalytic oxidative dehydrogenation process carried out at elevated pressures (10 barg) over platinum and palladium supported on a foam monolith or on a bed of alumina spheres. The hydrocarbon feeds exemplified are propane and naphtha. The total feed flow rates range from 2.1 SLPM at 1 bara to 280 SLPM at 11 bara, corresponding to superficial feed velocities of ~44 to ~240 cm s$^{-1}$ at standard temperature and operating pressure.

The use of higher superficial feed velocities provides the advantages that the auto-thermal cracking process may be carried out using a reduced number of reactors and also at a reduced risk of flashback.

Thus, it would be desirable to operate an auto-thermal cracking process using higher superficial feed velocities than have previously been used but without incurring significant deterioration in hydrocarbon feed conversion and olefin yield.

Accordingly, the present invention provides a process for the production of an olefin, said process comprising:

partially combusting in a reaction zone a mixture of a hydrocarbon and an oxygen-containing gas in the presence of a catalyst which is capable of supporting combustion beyond the fuel rich limit of flammability to produce the olefin, wherein the superficial feed velocity of said mixture is at least 300 cm s$^{-1}$ at standard temperature and operating pressure.

According to a second aspect of the present invention, there is provided a process for the production of an olefin, said process comprising:

partially combusting in a reaction zone a mixture of a hydrocarbon and an oxygen-containing gas in the presence of a catalyst which is capable of supporting combustion beyond the fuel rich limit of flammability to produce the olefin, wherein the superficial feed velocity of said mixture is at least 250 cm s$^{-1}$ at standard temperature and operating pressure and wherein the catalyst is supported on a catalyst support.

The superficial feed velocity of the hydrocarbon and oxygen-containing gas mixture may be any practical superficial feed velocity, but where the catalyst is an unsupported catalyst, is at least 300 cm s$^{-1}$ and where the catalyst is a supported catalyst, is at least 250 cm s$^{-1}$.

Preferably the superficial feed velocity of the hydrocarbon and oxygen-containing gas mixture is in the range 300 cm s$^{-1}$ to 5000 cm s$^{-1}$. More preferably the superficial feed velocity is in the range 500 to 3000 cm s$^{-1}$, even more preferably, in the range 600 to 2000 cm s$^{-1}$, and most preferably, in the range 600 to 1200 cm s$^{-1}$; for example, in the range 600 to 700 cm s$^{-1}$.

The hydrocarbon may be any hydrocarbon which can be converted to an olefin, preferably a mono-olefin, under the partial combustion conditions employed.

The process of the present invention may be used to convert both liquid and gaseous hydrocarbons into olefins. Suitable liquid hydrocarbons include naphtha, gas oils, vacuum gas oils and mixtures thereof Preferably, however, gaseous hydrocarbons such as ethane, propane, butane and mixtures thereof are employed. Suitably, the hydrocarbon is a paraffin-containing feed comprising hydrocarbons having at least two carbon atoms.

The hydrocarbon feed is mixed with any suitable oxygen-containing gas. Suitably, the oxygen-containing gas is molecular oxygen, air, and/or mixtures thereof. The oxygen-containing gas may be mixed with an inert gas such as nitrogen or argon.

Additional feed components may be included, if so desired. Suitably, methane, hydrogen, carbon monoxide, carbon dioxide or steam may be co-fed into the reactant stream.

Any molar ratio of hydrocarbon to oxygen-containing gas is suitable provided the desired olefin is produced in the process of the present invention. The preferred stoichiometric ratio of hydrocarbon to oxygen-containing gas is 5 to 16, preferably, 5 to 13.5 times, preferably, 6 to 10 times the stoichiometric ratio of hydrocarbon to oxygen-containing gas required for complete combustion of the hydrocarbon to carbon dioxide and water.

The hydrocarbon is passed over the catalyst at a gas hourly space velocity of greater than 10,000 h$^{-1}$, preferably above 20,000 h$^{-1}$ and most preferably, greater than 100,000 h$^{-1}$. It will be understood, however, that the optimum gas hourly space velocity will depend upon the pressure and nature of the feed composition.

Additionally, the use of a high superficial feed velocity in combination with a high gas hourly space velocity provides the advantage that the amount of catalyst and/or size of reactor(s) required to carry out the auto-thermal cracking process is minimised. Suitably, therefore, where the superficial feed velocity is above 300 cm/s, the gas hourly space velocity is preferably above 200,000/h.

In a preferred embodiment of the present invention, hydrogen is co-fed with the hydrocarbon and oxygen-containing gas into the reaction zone. The molar ratio of hydrogen to oxygen-containing gas can vary over any operable range provided that the desired olefin product is produced. Suitably, the molar ratio of hydrogen to oxygen-containing gas is in the range 0.2 to 4, preferably, in the range 1 to 3.

Advantageously, it has been found that the use of a hydrogen co-feed allows, for a given feed throughput, the use of higher superficial feed velocities than when the process is carried out in the absence of hydrogen.

Hydrogen co-feeds are also advantageous because, in the presence of the catalyst, the hydrogen combusts preferentially relative to the hydrocarbon, thereby increasing the olefin selectivity of the overall process.

Preferably, the reactant mixture of hydrocarbon and oxygen-containing gas (and optionally hydrogen co-feed) is preheated prior to contact with the catalyst. Generally, the reactant mixture is preheated to temperatures below the autoignition temperature of the reactant mixture.

Advantageously, a heat exchanger may be employed to preheat the reactant mixture prior to contact with the catalyst. The use of a heat exchanger may allow the reactant mixture to be heated to high preheat temperatures such as temperatures at or above the autoignition temperature of the reactant mixture. The use of high pre-heat temperatures is beneficial in that less oxygen reactant is required which leads to economic savings. Additionally, the use of high preheat temperatures can result in improved selectivity to olefin product. It has also be found that the use of high preheat temperatures enhances the stability of the reaction within the catalyst thereby leading to higher sustainable superficial feed velocities.

It should be understood that the autoignition temperature of a reactant mixture is dependent on pressure as well as the feed composition: it is not an absolute value. Typically, in auto-thermal cracking processes, where the hydrocarbon is ethane at a pressure of 2 atmospheres, a preheat temperature of up to 450° C. may be used.

The catalyst is any catalyst which is capable of supporting combustion beyond the fuel rich limit of flammability. Suitably, the catalyst may be a Group VIII metal. Suitable Group VIII metals include platinum, palladium, ruthenium, rhodium, osmium and iridium. Preferably, the Group VIII metal is rhodium, platinum, palladium or mixtures thereof. Especially preferred are platinum, palladium or mixtures thereof. Typical Group VIII metal loadings range from 0.01 to 100 wt %, preferably, from 0.1 to 20 wt %, and more preferably, from 0.5 to 10 wt %, for example 1-5 wt %, such as 3-5 wt %.

Where a Group VIII metal catalyst is employed, it is preferably employed in combination with at least one promoter. The promoter may be selected from elements of Groups IIIA, IVA and VA of the Periodic Table and mixtures thereof. Alternatively, the promoter may be a transition metal, which is different to the Group VIII metal(s) employed as the catalytic component.

Preferred Group IIIA metals include Al, Ga, In and Tl. Of these, Ga and In are preferred. Preferred Group IVA metals include Ge, Sn and Pb. Of these, Ge and Sn are preferred. The preferred Group VA metal is Sb. The atomic ratio of Group VIII metal to the Group IIIA, IVA or VA metal may be 1:0.1-50.0, preferably, 1:0.1-12.0, such as 1:0.3-5.

Suitable transition metal promoters may be selected from any one or more of Groups IB to VIII of the Periodic Table. In particular, transition metals selected from Groups IB, IIB, VIB, VIIB and VIIIB of the Periodic Table are preferred. Examples of such metals include Cr, Mo, W, Fe, Ru, Os, Co, Rh, Ir, Ni, Pt, Cu, Ag, Au, Zn, Cd and Hg. Preferred transition metal promoters are Mo, Rh, Ru, Ir, Pt, Cu and Zn. The atomic ratio of the Group VIII metal to the transition metal promoter may be 1:0.1-50.0, preferably, 1:0.1-12.0.

In one embodiment of the present invention, the catalyst comprises a single promoter metal selected from Group IIIA, Group IVA, Group VB and the transition metal series. For example, the catalyst may comprise as the catalytic component, rhodium, platinum or palladium and as a promoter a metal selected from the group consisting of Ga, In, Sn, Ge, Ag, Au or Cu. Preferred examples of such catalysts include Pt/Ga, Pt/In, Pt/Sn, Pt/Ge, Pt/Cu, Pd/Sn, Pd/Ge, Pd/Cu and Rh/Sn. Of these Pt/Cu and Pt/Sn are most preferred.

Where promoted Rh, Pd or Pt catalysts are employed, the Rh, Pt or Pd may form between 0.01 and 5.0 wt %, preferably, between 0.01 and 2.0 wt %, and more preferably, between 0.05 and 1.5 wt % of the total weight of the catalyst. The atomic ratio of Rh, Pt or Pd to the Group IIIA, IVA or transition metal promoter may be 1:0.1-50.0, preferably, 1:0.1-12.0. For example, atomic ratios of Rh, Pt or Pd to Sn may be 1:0.1 to 50, preferably, 1:0.1-12.0, more preferably, 1:0.2-4.0 and most preferably, 1:0.5-2.0. Atomic ratios of Pt or Pd to Ge, on the other hand, may be 1:0.1 to 50, preferably, 1:0.1-12.0, and more preferably, 1:0.5-8.0. Atomic ratios of Pt or Pd to Cu may be 1:0.1-3.0, preferably, 1:0.2-2.0, and more preferably, 1:0.3-1.5.

In another embodiment of the present invention, the promoter comprises at least two metals selected from Group IIIA, Group IVA and the transition metal series. For example, where the catalyst comprises platinum, it may be promoted with two metals from the transition metal series, for example, palladium and copper. Such Pt/Pd/Cu catalysts may comprise palladium in an amount of 0.01 to 5 wt %, preferably, 0.01 to 2 wt %, and more preferably, 0.01 to 1 wt %. The atomic ratio of Pt to Pd may be 1:0.1-10.0, preferably, 1:0.5-8.0, and more preferably, 1:1.0-5.0. The atomic ratio of platinum to copper is preferably 1:0.1-3.0, more preferably, 1:0.2-2.0, and most preferably, 1:0.5-1.5.

Alternatively, where the catalyst comprises platinum, it may be promoted with one transition metal, and another metal selected from Group IIIA or Group IVA of the periodic table. In such catalysts, palladium may be present in an amount of 0.01 to 5 wt %, preferably, 0.01 to 2.0 wt %, and more preferably, 0.05-1.0 wt % based on the total weight of such catalysts. The atomic ratio of Pt to Pd may be 1:0.1-10.0, preferably, 1:0.5-8.0, and more preferably, 1:1.0-5.0. The atomic ratio of Pt to the Group IIIA or IVA metal may be 1:0.1-60, preferably, 1:0.1-50.0. Preferably, the Group IIIA or IVA metal is Sn or Ge, most preferably, Sn.

For the avoidance of doubt, the Group VIII metal and the promoter in the catalyst may be present in any form, for example, as a metal, or in the form of a metal compound, such as an oxide.

It should be understood that the actual concentrations of metal in the catalysts tend not to be identical to the nominal concentrations employed in the preparation of the catalyst because not all of the metal employed during the preparation of the catalyst becomes incorporated into the final catalyst composition. Thus, the nominal metal concentrations may have to be varied to ensure that the desired actual metal concentrations are achieved.

The catalyst employed in the present invention may be unsupported. For example, the catalyst may be in the form of a metal gauze. Preferably, however, the catalyst employed in the process of the present invention may be a supported catalyst. Although a range of support materials may be used, ceramic supports are generally preferred. However, metal supports may also be used.

Suitably, the ceramic support may be any oxide or combination of oxides that is stable at high temperatures of, for example, between 600° C. and 1200° C. The ceramic support material preferably has a low thermal expansion co-efficient, and is resistant to phase separation at high temperatures.

Suitable ceramic supports include cordierite, lithium aluminium silicate (LAS), alumina (alpha-$Al_2O_3$), yttria stabilised zirconia, aluminium titanate, niascon, and calcium zirconyl phosphate.

The ceramic support may be wash-coated, for example, with gamma-$Al_2O_3$.

The structure of the support material is important, as the structure may affect flow patterns through the catalyst. Such flow patterns may influence the transport of reactants and products to and from the catalyst surface, thereby affecting the activity of the catalyst. Typically, the support material may be in the form of particles, such as spheres or other granular shapes or it may be in the form of a foam or fibre such as a fibrous pad or mat. Preferably, the form of the support is a monolith which is a continuous multi-channel ceramic structure. Such monoliths include honeycomb structures, foams, or fibrous pads. The pores of foam monolith structures tend to provide tortuous paths for reactants and products. Such foam monolith supports may have 20 to 80, preferably, 30 to 50 pores per inch. Channel monoliths generally have straighter, channel-like pores. These pores are generally smaller, and there may be 80 or more pores per linear inch of catalyst.

Preferred ceramic foams include lithium aluminium silicate.

Alternatively, the support may be present as a thin layer or wash coat on another substrate.

Preferred supports include gamma-alumina wash-coated lithium aluminium silicate foam and alumina spheres.

The catalyst employed in the present invention may be prepared by any method known in the art. For example, gel methods and wet-impregnation techniques may be employed. Typically, the support is impregnated with one or more solutions comprising the metals, dried and then calcined in air. The support may be impregnated in one or more steps. Preferably, multiple impregnation steps are employed. The support is preferably dried and calcined between each impregnation, and then subjected to a final calcination, preferably, in air. The calcined support may then be reduced, for example, by heat treatment in a hydrogen atmosphere.

The catalyst may be in the form of a fluidised or fixed bed. Preferably, a fixed bed catalyst is employed.

The process of the present invention may suitably be carried out at a catalyst exit temperature in the range 600° C. to 1200° C., preferably, in the range 850° C. to 1050° C. and, most preferably, in the range 900° C. to 1000° C.

The process of the present invention may be carried out at atmospheric or elevated pressure. Suitably, the pressure may be in the range from 0 to 2 bara, preferably 1.5 to 2 bara, for example 1.8 bara. Elevated pressures of, for example, 2 to 50 bara, may also be suitable.

Where the process of the present invention is carried out at elevated pressure, the reaction products may be quenched as they emerge from the reaction chamber to avoid further reactions taking place.

Any coke produced in the process of the present invention may be removed by mechanical means, or by using one of the decoking methods such as that described in EP-A-0 709 446, the contents of which are hereby incorporated by reference.

The degree of conversion of the hydrocarbon in the process of the present invention may be influenced by such factors as the nature of the feed composition, the process conditions, the catalyst composition, the reactor and, in particular, heat losses from the reactor. High heat losses can lead to lower hydrocarbon conversion as some of the energy generated by the exothermic combustion reaction is lost to the surroundings rather than being utilized to convert the hydrocarbon to olefin. External heating around the reaction zone can be employed to minimise heat losses and approach adiabatic operation. In the process of the present invention, the conversion of the hydrocarbon is generally at least 30 mole %, preferably, at least 50 mole %, more preferably, at least 60 mole %, such as at least 70 mole %.

The selectivity to olefin in the process of the present invention may vary depending on such factors as the nature of the feed composition, the process conditions, the composition of the catalyst and the reactor. In the process of the present invention, selectivity to olefin is typically at least 60 g per 100 g hydrocarbon converted, preferably, at least 70 g per 100 g hydrocarbon converted.

The invention will now be illustrated by way of example only and with reference to FIG. 1 and to the following examples.

FIG. 1 represents in schematic form, apparatus suitable for use in the process of the present invention.

FIG. 1 depicts an apparatus 10 comprising a quartz reactor 12 surrounded by an electrically-heated furnace 14. The reactor 12 is coupled to an oxygen-containing gas supply 16 and a hydrocarbon feed supply 18. Optionally, the hydrocarbon feed may comprise a co-feed such as hydrogen and a diluent such as nitrogen. In use, a catalyst which is capable of supporting combustion beyond the fuel rich limit of flammability 20 is located within the reactor 12. The catalyst 20 is placed between a pair of ceramic foam heat shields 22, 24.

The furnace 14 is set to minimise heat losses, and the reactants are introduced into the reactor via line 26. In use, as the reactants contact the catalyst 20, some of the hydrocarbon feed combusts to produce water and carbon oxides. The optional hydrogen co-feed also combusts to produce water. Both of these combustion reactions are exothermic, and the heat produced therefrom is used to drive the cracking of the hydrocarbon to produce olefin.

CATALYST PREPARATION EXPERIMENTS

Experiment 1

Preparation of Catalyst A (0.7 wt % Pt)

The catalyst was prepared by impregnating a lithium aluminium silicate foam support (30 pores per inch, ex Vesuvius Hi-Tech Ceramics Inc) having a high porosity alumina (HPA) wash-coat in a solution of $(NH_3)_4Pt^{II}Cl_2$. The $(NH_3)_4Pt^{II}Cl_2$ solution was prepared with sufficient salt to achieve a nominal Pt loading of 0.7 wt %. The quantity of salt employed was that which would achieve the final target loading if 100% of the platinum metal in the salt was taken up by the support material. The $(NH_3)_4Pt^{II}Cl_2$ was dissolved in a volume of de-ionised water equivalent to three times the bulk volume of the support material. The support was impregnated with the platinum solution, dried in air at 120° C. for ca. 30 minutes, then calcined in air at 450° C. for a further 30 minutes. The support was then allowed to cool to room temperature and the impregnation-drying-calcination cycle was repeated until all of the platinum solution had been absorbed on to the support (3-4 cycles were required.). The catalyst was then calcined in air at 1200° C. for 6 hours (the temperature being increased from 450° C. to 1200° C. at 2° C./min).

Experiment 2

Preparation of Catalyst B (3 wt % Pt)

The procedure of Experiment 1 was repeated using a $(NH_3)_4Pt^{II}Cl_2$ solution of sufficient concentration to achieve a nominal Pt loading of 3 wt %.

Experiment 3

Preparation of Catalyst C (5 wt % Pt)

The procedure of Experiment 1 was repeated using a $(NH_3)_4Pt^{II}Cl_2$ solution of sufficient concentration to achieve a nominal Pt loading of 5 wt %.

Experiment 4

Preparation of Catalyst D (3 wt % Pt, 1 wt % Cu)

The catalyst was prepared by impregnating a lithium aluminium silicate foam support (30 pores per inch, ex Vesuvius Hi-Tech Ceramics Inc) having an HPA wash-coat with a solution of 1) $(NH_3)_4Pt^{II}Cl_2$, and 2) $Cu(NO_3)_2$. Prior to the impregnation process the LAS-HPA foam support was calcined in air at 1200° C.

Solutions of $(NH_3)_4Pt^{II}Cl_2$, and $Cu(NO_3)_2$ in de-ionised water were prepared with sufficient salt to achieve nominal Pt and Cu loadings of 3 wt % and 1 wt %, respectively. The quantity of salt dissolved was equivalent to that needed to achieve the final target platinum and copper loading if 100% of the platinum and copper were to be recovered on the final catalyst. The volumes of de-ionised water used for the solutions were equal to three times the bulk volume of the support material.

The support was alternately impregnated with the platinum- and copper-containing solutions. Between each impregnation the support was dried in air at 120° C. for ca. 30 minutes, calcined in air at 450° C. for a further 30 minutes, then cooled to room temperature for the subsequent impregnation. The impregnation-drying-calcination cycles were repeated until all the impregnation solutions had been absorbed onto the support.

The impregnated support was then dried, and then finally calcined in air for 6 hours at 600° C. Immediately prior to use in the auto-thermal cracking reaction the catalyst was reduced in-situ using ca. 2 nl/min of hydrogen and 2 nl/min of nitrogen. The reduction temperature was maintained for 1 hour at 750° C.

Experiment 5

Preparation of Catalyst E (3 wt % Pt, 1 wt % Cu)

The procedure of Experiment 4 was repeated, except that the final calcination in air was carried out at 1200° C.

Experiment 6

Preparation of Catalyst F (3 wt % Pt, 1 wt % Cu)

The procedure of Experiment 4 was repeated, except that the final calcinations in air was carried out at 1200° C., and the reduction step was omitted.

Experiment 7

Preparation of Catalyst G (2 wt % Pt, 4 wt % Sn)

The procedure of Experiment 4 was repeated using a $(NH_3)_4Pt^{II}Cl_2$ solution of sufficient concentration to give a nominal Pt loading of 2 wt % and a $SnCl_2$/dil HCl solution of sufficient concentration to give a nominal Sn loading of 4 wt %.

Experiment 8

Preparation of Catalyst H (4 wt % Pt, 4 wt % Sn)

The procedure of Experiment 4 was repeated using a $(NH_3)_4Pt^{II}Cl_2$ solution of sufficient concentration to give a nominal Pt loading of 4 wt % and a $SnCl_2$/dil HCl solution of sufficient concentration to give a nominal Sn loading of 4 wt %.

EXAMPLE 1

Auto-thermal Cracking of Ethane in the Presence of Hydrogen at Atmospheric Pressure The catalysts A to H as prepared in Experiments 1 to 8 above and having dimensions 15 mm diameter by 30 mm depth, a porosity of 30 pores per inch and a volume of 5.30 $cm^3$ were placed in an apparatus as described for FIG. 1. The reactor had an internal diameter of 15 mm. Oxygen, ethane, hydrogen and nitrogen as diluent (10 vol %) were contacted with the catalyst under the conditions shown in Table 1 below. The ratio of hydrogen to oxygen was 2:1 (v/v); the oxygen:ethane feed ratio was 0.65 (wt/wt) (1.00:2.04 v/v). The reaction was carried out at atmospheric pressure.

The product composition was analysed by gas chromatography fitted with thermal conductivity and flame ionization detectors. Gas feed rates were controlled by thermal mass flow controllers (ex Bronkhorst HiTec).

The electrically-heated furnace surrounding the reactor and catalyst was set to 850° C. to minimise heat losses from the catalyst/reaction zone.

From analysis of the feed and product flow rates and compositions the following parameters were calculated:

Conversion

Ethane conversion %=ethane feed (g/min)–ethane in effluent (g/min)/ethane feed (g/min)*100

Oxygen conversion %=oxygen feed (g/min)–oxygen in effluent (g/min)/oxygen feed (g/min)*100

Change in ethane conversion (%/(cm/s))=(ethane conversion @ higher velocity)–(ethane conversion @ lower velocity)/higher velocity (cm/s)–lower velocity (cm/s)

Change in oxygen conversion (%/(cm/s))=(oxygen conversion @ higher velocity)–(oxygen conversion @ lower velocity)/higher velocity (cm/s)–lower velocity (cm/s)

Selectivity $$\text{Ethylene selectivity (g per 100 g ethane converted)} = 100 \times \frac{\text{ethylene in product (g/min)}}{\text{ethane in feed (g/min)} - \text{ethane in product (g/min)}}$$

Yield $$\text{Ethylene selectivity (g per 100 g ethane feed)} = 100 \times \frac{\text{ethylene in product (g/min)}}{\text{ethane in feed (g/min)}}$$

The results are given in Table 1.

Table 1 clearly shows that the decrease in conversion to olefin on increasing the superficial feed velocity from approximately 200 to 670 cm s$^{-1}$ is relatively small.

TABLE 1

|  |  | Catalyst A (0.7 wt % Pt) | | Catalyst B (3 wt % Pt) | | Catalyst C (5 wt % Pt) | | Catalyst D (3 wt % Pt, 1 wt % Cu) | |
| --- | --- | --- | --- | --- | --- | --- | --- | --- | --- |
| feed temperature | ° C. | 195 | 119 | 208 | 133 | 186 | 132 | 222 | 136 |
| cat face temp | ° C. | 546 | 233 | 663 | 408 | 882 | 631 | 1034 | 746 |
| cat exit temp | ° C. | 940 | 795 | 921 | 837 | 903 | 860 | 955 | 966 |
| adiabatic temp | ° C. | 790 | 664 | 799 | 690 | 783 | 687 | 811 | 749 |

TABLE 1-continued

| | | | | | | | | | |
|---|---|---|---|---|---|---|---|---|---|
| cat face temp change | ° C. | | −313 | | −255 | | −251 | | −288 |
| cat exit temp change | ° C. | | −145 | | −84 | | −43 | | 11 |
| heat loss | % | 13.08 | 31.03 | 10.28 | 24.83 | 11.09 | 24.25 | 10.29 | 19.55 |
| feed rates | | | | | | | | | |
| Total feed rate | nl/min | 22.03 | 71.67 | 22.20 | 71.23 | 22.30 | 70.89 | 22.18 | 70.82 |
| GSHV | /h | 249329 | 811138 | 251253 | 806159 | 252384 | 802311 | 251026 | 801518 |
| Superficial gas velocity at standard temperature and operating pressure | cm/s | 208 | 676 | 209 | 672 | 210 | 669 | 209 | 668 |
| conversions | | | | | | | | | |
| ethane | % | 76.08 | 35.5 | 78.39 | 44.24 | 74.25 | 43.12 | 81.24 | 63.45 |
| oxygen | % | 98.3 | 84.93 | 96.53 | 83.19 | 95.98 | 81.32 | 98.31 | 94.85 |
| change in conversion | | | | | | | | | |
| ethane | % per cm/s | 8.67 | | 7.39 | | 6.79 | | 3.88 | |
| oxygen | % per cm/s | 2.86 | | 2.88 | | 3.20 | | 0.75 | |
| Ethylene yield | (g/100 g ethane feed) | 52.60 | 24.98 | 53.73 | 31.78 | 51.27 | 31.66 | 56.64 | 47.34 |
| Ethylene selectivity | (g/100 g ethane converted) | 69.13 | 70.37 | 68.55 | 71.84 | 69.05 | 73.42 | 69.73 | 74.60 |

| | | Catalyst E (3 wt % Pt, 1 wt % Cu) | | Catalyst F (3 wt % Pt, 1 wt % Cu) | | Catalyst G (2 wt % Pt, 4 wt % Sn) | | Catalyst H (4 wt % Pt, 4 wt % Sn) | |
|---|---|---|---|---|---|---|---|---|---|
| feed temperature | ° C. | 232 | 119 | 186 | 121 | 161 | 138 | 208 | 127 |
| cat face temp | ° C. | 1033 | 778 | 971 | 621 | 901 | 350 | 1032 | 690 |
| cat exit temp | ° C. | 950 | 901 | 950 | 930 | 937 | 969 | 967 | 958 |
| adiabatic temp | ° C. | 814 | 748 | 809 | 742 | 807 | 776 | 810 | 741 |
| cat face temp change | ° C. | | −255 | | −350 | | −551 | | −342 |
| cat exit temp change | ° C. | | −49 | | −20 | | 32 | | −9 |
| heat loss | % | 9.44 | 17.07 | 7.96 | 19.36 | 9.75 | 11.52 | 9.94 | 18.55 |
| feed rates | | | | | | | | | |
| Total feed rate | nl/min | 22.18 | 70.76 | 22.16 | 71.15 | 17.72 | 69.41 | 22.15 | 70.84 |
| GSHV | /h | 251026 | 800839 | 250800 | 805253 | 200549 | 785561 | 250687 | 801745 |
| Superficial gas velocity at standard temperature and operating pressure | cm/s | 209 | 667 | 209 | 671 | 167 | 655 | 209 | 668 |
| conversions | | | | | | | | | |
| ethane | % | 82.23 | 62.96 | 80.77 | 60.94 | 79.66 | 71.31 | 80.76 | 60.59 |
| oxygen | % | 97.86 | 92.86 | 97.81 | 93.23 | 98.88 | 94.52 | 98.08 | 91.5 |
| change in conversion | | | | | | | | | |
| ethane | % per cm/s | 4.21 | | 4.29 | | 1.71 | | 4.39 | |
| oxygen | % per cm/s | 1.09 | | 0.99 | | 0.89 | | 1.43 | |
| Ethylene yield | (g/100 g ethane feed) | 56.84 | 47.08 | 56.49 | 45.65 | 57.15 | 52.16 | 56.14 | 45.24 |
| Ethylene selectivity | (g/100 g ethane converted) | 69.12 | 74.78 | 69.94 | 74.91 | 71.74 | 73.15 | 69.52 | 74.66 |

Experiment 9

Preparation of Catalyst I (3 wt % Pt)

The catalyst was prepared by impregnating alumina spheres (1.8 mm diameter, ex Condea) with a solution of (NH3)4PtIICl2. Prior to impregnation the spheres were calcined in air to 1200° C. for 6 hours to remove any residual porosity.

A solution of (NH3)4PtIICl2 in de-ionised water was prepared with sufficient salt to achieve a nominal Pt loading of 3 wt %. The quantity of salt dissolved was equivalent to that needed to achieve the final target platinum loading if 100% of the platinum were to be recovered on the final catalyst. The volume of de-ionised water used for the solution was equal to the bulk volume of the support material.

The support was impregnated with the platinum solution, dried in air at 120° C. for ca. 30 minutes, then calcined in air at 450° C. for a further 30 minutes and then cooled to room temperature. The impregnation-drying-calcination cycle was repeated until all of the platinum solution had been absorbed on to the support (1-2 cycles were required.). After the final calcination at 450° C., the catalyst was further calcined in air at 1200° C. for 6 hours (the temperature being increased from 450° C. to 1200° C. at 5° C./min) and then allowed to cool to room temperature.

Experiment 10

Preparation of Catalyst J (3 wt % Pt, 1 wt % Cu)

The catalyst was prepared by impregnating alumina spheres (1.8 mm diameter, ex Condea) with solutions of I) (NH3)4PtIICl2 and 2) Cu(NO3)2. Prior to impregnation the spheres were calcined in air to 1200° C. for 6 hours to remove any residual porosity.

Solutions of $(NH_3)_4Pt^{II}Cl_2$, and $Cu(NO_3)_2$ in de-ionised water were prepared with sufficient salt to achieve nominal Pt and Cu loadings of 3 wt % and 1 wt %, respectively. The quantity of salt dissolved was equivalent to that needed to achieve the final target platinum and copper loading if 100% of the platinum and copper were to be recovered on the final catalyst. The volumes of de-ionised water used for the solutions were equal to the bulk volume of the support material.

The support was alternately impregnated with the platinum and copper solutions. Between each impregnation the support was dried in air at 120° C. for ca. 30 minutes, calcined in air at 450° C. for a further 30 minutes, then cooled to room temperature for the subsequent impregnation. The impregnation-drying-calcination cycles were repeated until all of the impregnation solutions had been absorbed onto the support.

After the final calcination at 450° C., the catalyst was further calcined in air at 600° C. for 6 hours (the temperature being increased from 450° C. to 600° C. at 5° C./min) and then allowed to cool to room temperature.

Prior to use in the auto-thermal cracking reaction the catalyst was reduced using ca. 2 nl/min of hydrogen and 2 nl/min of nitrogen and at a temperature of 750° C. This reduction temperature was maintained for 1 hour after which the catalyst was allowed to cool to room temperature under nitrogen and then transferred to the reactor.

Experiment 11

Preparation of Catalyst K (1 wt % Pt, 4 wt % Sn)

The procedure of Experiment 10 was repeated using a $(NH_3)_4P^{II}Cl_2$ solution of sufficient concentration to give a nominal Pt loading of 1 wt % and a $SnCl_2$/dil HCl solution of sufficient concentration to give a nominal Sn loading of 4 wt %.

Experiment 12

Preparation of Catalyst L (3 wt % Pt)

The catalyst was prepared by the procedure of Experiment 9 except that a lithium aluminium silicate foam support (30 pores per inch, ex Vesuvius Hi-Tech Ceramics Inc) was used in place of the alumina and the $(NH_3)_4Pt^{II}Cl_2$ was dissolved in a volume of de-ionised water equivalent to three times the bulk volume of the support material.

Experiment 13

Preparation of Catalyst M (3 wt % Pt, 1 wt % Cu)

The procedure of Experiment 10 was repeated using a (NH3)4PtIICl2 solution of sufficient concentration to give a nominal loading of 3 wt % Pt and a $Cu(NO_3)_2$ solution of sufficient concentration to give a nominal loading of 1 wt % Cu. In addition the alumina spheres were replaced by a lithium aluminium silicate foam (30 pores per inch, ex Vesuvius Hi-Tech Ceramics Inc) and the volumes of de-ionised water used for the platinum and copper solutions were equivalent to three times the bulk volume of the support material.

EXAMPLE 2

Auto-thermal Cracking of Ethane in the Presence of Hydrogen at Elevated Pressure The catalysts I to K as prepared in Experiments 9 to 11 above and having dimensions 15 mm diameter by 60 mm depth, and a volume of 10.60 cm³ were placed in a metallic reactor (internal diameter 15 mm) with a quartz lining and fitted with a pressure jacket. Catalysts I to K were tested as packed beds of spheres supported on an alumina foam block of dimensions 15 mm diameter, 10 mm depth and of porosity 30 pores per inch.

Catalyst L as prepared in Experiment 12 above was tested as a ceramic foam bed within a metallic reactor fitted with a pressure jacket (bed diameter 18 mm, bed depth 60 mm, bed volume 15.27 cm³).

Catalyst M as prepared in Experiment 13 above was tested as a ceramic foam bed in a quartz lined metallic reactor fitted with a pressure jacket (bed diameter 15 mm, bed depth 60 mm, bed volume 10.60 cm³).

The pressure jacket was not externally heated.

The catalysts (I-M) were heated to approximately 200° C. under nitrogen at reaction pressure. Oxygen, ethane, hydrogen and nitrogen as diluent (10 vol %) pre-heated to 180-200° C. were then contacted with the catalyst under the conditions shown in Table 2 below. The ratio of hydrogen to oxygen was 2:1 (v/v); the oxygen:ethane feed ratio for catalysts I-K and M was 1.00:1.77 v/v; the oxygen: ethane feed ratio for catalyst K was 1.00:2.34 v/v. The reaction pressures are shown in Table 2.

The product composition was analysed by gas chromatography fitted with thermal conductivity and flame ionization detectors. Gas feed rates were controlled by thermal mass flow controllers (ex Bronkhorst HiTec BV)

From analysis of the feed and product flow rates and compositions, the ethane and oxygen conversions, ethylene selectivity and yield were calculated using the equations given in Example 1.

TABLE 2

| | Catalyst I (3 wt % Pt) | | Catalyst J (3 wt % Pt, 1 wt % Cu) | | Catalyst K (1 wt % Pt, 4 wt % Sn) | | Catalyst L (3 wt % Pt) | | Catalyst M (3 wt % Pt, 1 wt % Cu) | |
|---|---|---|---|---|---|---|---|---|---|---|
| preheat temperature (° C.) | 186 | 191 | 191 | 194 | 178 | 195 | 217 | 257 | 164 | 186 |
| cat face temp (° C.) | 925 | 900 | 1041 | 1045 | 1054 | 1045 | 298 | 300 | 340 | 265 |
| cat exit temp (° C.) | 898 | 944 | 944 | 990 | 886 | 1019 | 911 | 897 | 850 | 969 |
| temp change front | | −25 | | 4 | | −9 | | 2 | | −75 |
| temp change base | | 46 | | 46 | | 133 | | −14 | | 119 |
| adiabatic temp | 717 | 799 | 794 | 820 | 766 | 854 | 738 | 770 | 707 | 804 |
| heat loss % | 39.47 | 18.58 | 24.50 | 16.10 | 33.74 | 10.14 | 15.50 | 16.14 | 42.03 | 23.16 |
| pressure (bara) | 1.3 | 1.3 | 1.3 | 1.44 | 1.3 | 1.3 | 1.8 | 1.8 | 1.3 | 1.3 |
| feed rates | | | | | | | | | | |
| total (nl/min) | 40.00 | 109.74 | 94.68 | 147.81 | 38.46 | 144.16 | 104.59 | 257.02 | 35.61 | 123.62 |
| GSHV (/h) | 226354 | 621001 | 535779 | 836433 | 217639 | 815779 | 411013 | 1010025 | 201511 | 699546 |
| superficial gas velocity* (cm/s) | 290 | 796 | 687 | 968 | 279 | 1046 | 381 | 935 | 258 | 897 |
| conversions | | | | | | | | | | |
| ethane (%) | 56.14 | 79.98 | 77.78 | 84.7 | 69.44 | 92.68 | 65.7 | 67.56 | 52.99 | 50.75 |
| oxygen (%) | 95.86 | 94.52 | 97.02 | 96.82 | 98.41 | 98.06 | 96.98 | 95.97 | 95.98 | 95.19 |
| ethylene yield (g per 100 g ethane feed) | 41.36 | 52.39 | 54.07 | 55.13 | 52.11 | 55.91 | 44.21 | 44.03 | 38.84 | 49.27 |
| ethylene selectivity (g per 100 g ethane converted) | 73.68 | 65.84 | 69.51 | 65.09 | 75.04 | 60.33 | 67.30 | 65.16 | 73.30 | 61.01 |

*at standard temperature and operating pressure

From Table 2 it is evident that the use of superficial feed velocities above 250 cm/s with supported catalysts produces acceptable ethylene conversions and yields. It can be seen that in these examples the heat loss at the lower superficial feed velocities is large (no external heating to compensate for losses to the immediate environment of the catalyst). As the superficial feed velocity is increased the heat losses decline and the losses to the environment become less significant as a fraction of the enthalpy of the products. As a consequence ethane conversion is seen to rise and ethylene yields are maintained.

Experiments 14-15

Preparation of Catalysts N and P

Catalysts N and P were each prepared by the procedure of Experiment 10 except that (i) solutions of (NH3)4PtIICl2, and (NH3)4PdIICl2 of sufficient concentration to achieve nominal Pt and Pd loadings for each catalyst as given in Table 3 were used (ii) a lithium aluminium silicate foam support (30 pores per inch, ex Vesuvius Hi-Tech Ceramics Inc) was used in place of the alumina spheres, iii) the volumes of de-ionised water used for the platinum and palladium solutions were equal to three times the bulk volume of the support material and (iv) there was no hydrogen reduction treatment.

EXAMPLE 3

Auto-thermal Cracking of Ethane in the Absence of Hydrogen at Atmospheric Pressure The catalysts N and P as prepared in Experiments 14 and 15 above and having dimensions and a volume as shown in Table 3 were placed in a metallic reactor (internal diameter 15 mm) with a quartz lining. Oxygen, ethane, and nitrogen were then contacted with the catalyst under the conditions shown in Table 3 below. The reaction was carried out at atmospheric pressure.

The product composition was analysed by gas chromatography fitted with thermal conductivity and flame ionization detectors. Gas feed rates were controlled by thermal mass flow controllers (ex Bronkhorst HiTec BV)

From analysis of the feed and product flow rates and compositions the ethane and oxygen conversions, ethylene selectivity and yield were calculated using the equations given in Example 1.

TABLE 3

| | Catalyst N | | Catalyst P | |
|---|---|---|---|---|
| Pt (wt %) | 0.23 | 0.23 | 2.06 | 2.06 |
| Pd (wt %) | 0.11 | 0.11 | 0.38 | 0.38 |
| Catalyst volume (cm3) | 5.30 | 5.30 | 5.30 | 5.30 |

TABLE 3-continued

|  | Catalyst N | | Catalyst P | |
| --- | --- | --- | --- | --- |
| Catalyst depth (mm) | 30 | 30 | 30 | 30 |
| Catalyst diameter (mm) | 15 | 15 | 15 | 15 |
| Preheat temperature (° C.) | 150 | 150 | 150 | 150 |
| Cat face temp (° C.) | 562 | 409 | 544 | 531 |
| Cat exit temp (° C.) | 853 | 886 | 828 | 996 |
| Temp change front (° C.) |  | −153 |  | −13 |
| Temp change exit (° C.) |  | 33 |  | 168 |
| Adiabatic temp (° C.) | 712 | 786 | 701 | 894 |
| Heat loss (%) | 29.86 | 10.41 | 31.72 | 10.35 |
| Ethane:oxygen (v/v) | 1.93 | 1.96 | 1.93 | 1.59 |
| Nitrogen:oxygen (v/v) | 0.42 | 0.43 | 0.42 | 0.15 |
| Total feed rate (nl/min) | 13.63 | 38.99 | 13.63 | 38.98 |
| GHSV (/h) | 154260 | 441277 | 154260 | 441163 |
| Superficial gas velocity* (cm/s) | 129 | 368 | 129 | 368 |
| Ethane conversion (%) | 67.68 | 83.28 | 61.02 | 98.61 |
| Oxygen conversion (%) | 98.62 | 98.54 | 98.8 | 99.66 |
| Ethylene yield (g per 100 g ethane feed) | 39.26 | 47.84 | 37.44 | 35.71 |
| Ethylene selectivity (g per 100 g ethane converted) | 58.15 | 57.32 | 60.17 | 36.17 |

*at standard temperature and operating pressure

The invention claimed is:

1. A process for the production of an olefin, said process comprising:
partially combusting in a reaction zone a mixture of a hydrocarbon and an oxygen-containing gas in the presence of a catalyst which is capable of supporting combustion beyond the fuel rich limit of flammability to produce the olefin, wherein the superficial feed velocity of said mixture is at least 300 cm s$^{-1}$ at standard temperature and operating pressure, and wherein the process is carried out at elevated pressure.

2. A process according to claim 1 wherein the superficial feed velocity of the hydrocarbon and oxygen-containing gas mixture is in the range 300 to 5000 cm/s.

3. A process according to claim 1 or claim 2 wherein the hydrocarbon is a paraffin-containing hydrocarbon feed having at least two carbon atoms.

4. A process according to claim 3 in which the hydrocarbon is selected from the group consisting of ethane, propane, butane, naphtha, gas oil, vacuum gas oil and mixtures thereof.

5. A process according to claim 1 wherein the molar ratio of hydrocarbon to the oxygen-containing gas is 5 to 16 times the stoichiometric ratio of hydrocarbon to oxygen-containing gas required for complete combustion to carbon dioxide and water.

6. A process according to claim 1 in which hydrogen is co-fed into the reaction zone.

7. A process according to claim 6 in which the molar ratio of hydrogen to oxygen-containing gas is in the range 0.2 to 4.

8. A process according to claim 1 wherein the process is conducted at a gas hourly space velocity of greater than 10,000/h.

9. A process according to claim 1 in which the catalyst comprises a Group VIII metal.

10. A process according to claim 9 wherein the Group VIII metal is selected from the group consisting of rhodium, platinum, palladium and mixtures thereof.

11. A process according to claim 9 or claim 10 in which the Group VIII metal catalyst comprises at least one promoter.

12. A process according to claim 11 wherein the at least one promoter is selected from the group consisting of elements of Groups IIIA, IVA, VA of the Periodic Table and mixtures thereof and a transition metal which is a different metal to the Group VIII metal employed as catalyst.

13. A process according to claim 12 wherein the promoter is selected from the group consisting of tin and copper.

14. A process according to claim 11 wherein the Group VIII metal is platinum and the promoter is selected from the group consisting of tin and copper.

15. A process according to claim 11 wherein the atomic ratio of Group VIII metal to promoter is in the range 1:0.1-50.0.

16. A process according to claim 1 wherein the catalyst is supported.

17. A process according to claim 16 wherein the support is a ceramic support.

18. A process according to claim 17 wherein the support is in the form of a monolith or particles.

19. A process according to claim 18 wherein the monolith is a foam or a fibre.

20. A process according to claim 1 in which the hydrocarbon and oxygen-containing gas mixture is preheated to a temperature below the auto-ignition temperature of the mixture.

* * * * *